United States Patent [19]

Teplicki

[11] Patent Number: 4,657,935

[45] Date of Patent: Apr. 14, 1987

[54] REAL ACNE CONTROL (RAC)

[76] Inventor: Carlos Teplicki, 20310 NE. 2nd Ave. #K14, N. Miami, Fla. 33179

[21] Appl. No.: 757,806

[22] Filed: Jul. 22, 1985

[51] Int. Cl.$^4$ .................. A61K 7/16; A61K 33/00; A61K 33/18

[52] U.S. Cl. .................. 514/724; 424/49; 424/52; 424/127; 424/150; 514/859; 514/901

[58] Field of Search .................. 424/49, 52, 127, 150; 514/859, 901

[56] References Cited

U.S. PATENT DOCUMENTS

| | | | |
|---|---|---|---|
| 3,530,217 | 9/1970 | White et al. | 514/859 |
| 4,085,217 | 4/1978 | Kalopissis | 514/859 |
| 4,340,628 | 7/1982 | Gilbertson et al. | 424/49 |
| 4,367,218 | 1/1983 | Jacobson | 424/49 |
| 4,420,471 | 12/1983 | Elton et al. | 424/49 |
| 4,479,939 | 10/1984 | Eckert et al. | 514/859 |
| 4,548,809 | 10/1985 | Fung et al. | 424/52 |

FOREIGN PATENT DOCUMENTS

| | | | |
|---|---|---|---|
| 60-152415 | 8/1985 | Japan | 514/859 |
| 2144326 | 3/1985 | United Kingdom | 514/859 |
| 2153224 | 8/1985 | United Kingdom | 514/859 |

Primary Examiner—Ronald W. Griffin

[57] ABSTRACT

The product which I have invented controls acne on the face and neck areas. It is most effective on infectious, cystic acne, the most serious type of acne. The product which I call Real Acne Control (RAC) is a mixture of 55% water and 45% alcohol. RAC is to be used inside the mouth and throat in a rinsing and gargling fashion without swallowing the mixture. The product is never applied to the outside of the face or throat.

The product works because human skin is a permeable membrane and by killing the bacteria in the inner mouth and throat, infections such as acne on the skin surface, are lessened.

3 Claims, No Drawings

REAL ACNE CONTROL (RAC)

The product which I have invented controls acne on the face and neck areas. The product works satisfactorily on all types of acne but is highly effective on cystic acne, the most infectious and most scarring type of acne.

The product is a mixture of 55% water and 45% alcohol. By rinsing and gargling three times a day with the product, a person with cystic acne will significantly improve their complexion. More frequent use of the product produces better results. The product is never swallowed and the product is never applied to the outside of the face or throat.

The reason the product works is that cystic acne is caused by an infection under the superficial layer of the skin. The origin of the infection is the inside of the mouth and throat. The skin is a permeable membrane and as a result the infection in the mouth and throat is communicated through the skin to the surface and acne is the result.

Washing one's face on the outside will not clear an acne infection because what needs washing is the inside of the mouth and throat. The mixture of 55% water and 45% alcohol if used as suggested, does the washing and kills the bacteria in the mouth and throat and clears the complexion.

Real Acne Control is a mixture that clears cystic acne in the facial cheeks and throat areas; other infected areas of the face also clear up if they are secondary infections and not originating from lung or sinus infections.

I claim:

1. The process of treating acne on the outside of the face and throat of human beings affected with acne which comprises using a mixture comprised of alcohol and water inside the mouth and throat in a rinsing and gargling fashion.

2. The process as recited in claim 1 wherein substances selected from the group consisting of flavorings, colorings, sweetners, stabilizers, bromides, iodides or flourides can be added to the mixture.

3. The process as recited in claim 1 wherein the vehicle for the mixture is selected from the group consisting of oral rinses and mouthwashes.

* * * * *